(12) United States Patent
Paukshto et al.

(10) Patent No.: US 10,065,046 B2
(45) Date of Patent: Sep. 4, 2018

(54) CONDUCTIVE BIOPOLYMER IMPLANT FOR ENHANCING TISSUE REPAIR AND REGENERATION USING ELECTROMAGNETIC FIELDS

(75) Inventors: Michael Paukshto, Foster City, CA (US); George Martin, Rockville, MD (US); John Cooke, Palo Alto, CA (US)

(73) Assignee: Fibralign Corporation, Union City, CA (US)

( * ) Notice: Subject to any disclaimer, the term of this patent is extended or adjusted under 35 U.S.C. 154(b) by 247 days.

(21) Appl. No.: 13/184,313

(22) Filed: Jul. 15, 2011

(65) Prior Publication Data

US 2012/0065703 A1 Mar. 15, 2012

Related U.S. Application Data (60) Provisional application No. 61/364,759, filed on Jul. 15, 2010.

(51) Int. Cl.
*A61N 1/00* (2006.01)
*A61N 1/40* (2006.01)
(Continued)

(52) U.S. Cl.
CPC .............. *A61N 1/40* (2013.01); *A61F 13/00* (2013.01); *A61L 27/446* (2013.01); *A61L 27/50* (2013.01); *A61L 27/54* (2013.01); *A61L 31/128* (2013.01); *A61F 2/04* (2013.01); *A61F 2/06* (2013.01); *A61F 2/28* (2013.01); *A61F 2/82* (2013.01); *A61F 13/00012* (2013.01); *A61F 13/00029* (2013.01); *A61F 13/00063* (2013.01); *A61F 2013/00089* (2013.01); *A61F 2013/00157* (2013.01); *A61F 2013/00221* (2013.01);
(Continued)

(58) Field of Classification Search
CPC ................ A61L 27/446; A61L 31/128; A61L 2300/102; A61L 2300/104; A61F 2013/00234; A61N 1/40
See application file for complete search history.

(56) References Cited

U.S. PATENT DOCUMENTS 4,060,081 A * 11/1977 Yannas et al. ............. 623/15.12
4,478,630 A    10/1984 Lambert
(Continued)

FOREIGN PATENT DOCUMENTS

EP    0 518 697 A2    12/1992
JP    59-501319    7/1984
(Continued)

OTHER PUBLICATIONS

Wikipedia. "Units of textile measurement". Downloaded from <http://en.wikipedia.org/wiki/Units_of_textile_measurement> on Feb. 13, 2015.*
(Continued)

*Primary Examiner* — Andrew Iwamaye
(74) *Attorney, Agent, or Firm* — Nixon Peabody LLP (57) ABSTRACT

Embodiments of the present invention relate generally to the field of tissue repair and regeneration. More specifically, embodiments of the present invention relate to medical devices, materials or constructs, such as conductive biocompatible polymers having one or more networks of metal nanowires that enhance tissue repair and regeneration using electromagnetic fields.

15 Claims, 4 Drawing Sheets

(51) Int. Cl.

| | | |
|---|---|---|
| *A61L 31/12* | (2006.01) | |
| *A61L 27/44* | (2006.01) | |
| *A61L 27/50* | (2006.01) | |
| *A61L 27/54* | (2006.01) | |
| *A61F 2/28* | (2006.01) | |
| *A61F 13/00* | (2006.01) | |
| *A61F 2/82* | (2013.01) | |
| *A61F 2/04* | (2013.01) | |
| *A61F 2/06* | (2013.01) | |
| *A61N 1/375* | (2006.01) | |

(52) U.S. Cl.
CPC .............. *A61F 2013/00225* (2013.01); *A61F 2013/00234* (2013.01); *A61F 2210/0004* (2013.01); *A61F 2210/0076* (2013.01); *A61F 2230/0019* (2013.01); *A61F 2230/0021* (2013.01); *A61F 2230/0069* (2013.01); *A61F 2250/0001* (2013.01); *A61F 2250/0015* (2013.01); *A61F 2250/0031* (2013.01); *A61F 2250/0032* (2013.01); *A61F 2250/0043* (2013.01); *A61L 2300/102* (2013.01); *A61L 2300/104* (2013.01); *A61L 2300/404* (2013.01); *A61L 2400/12* (2013.01); *A61N 1/375* (2013.01)

(56) References Cited

U.S. PATENT DOCUMENTS

| | | | |
|---|---|---|---|
| 4,544,516 A | | 10/1985 | Hughes et al. |
| 4,759,354 A * | | 7/1988 | Quarfoot .................. 602/50 |
| 4,869,200 A | | 9/1989 | Euverard |
| 4,902,508 A | | 2/1990 | Badylak et al. |
| 5,171,273 A | | 12/1992 | Silver et al. |
| 5,744,545 A | | 4/1998 | Rhee et al. |
| 5,922,028 A | | 7/1999 | Plouhar et al. |
| 6,087,549 A * | | 7/2000 | Flick ....................... 602/41 |
| 6,544,762 B1 | | 4/2003 | Tranquillo et al. |
| 6,592,623 B1 | | 7/2003 | Bowlin et al. |
| 6,737,053 B1 | | 5/2004 | Goh et al. |
| 6,808,791 B2 * | | 10/2004 | Curro ..................... A47L 1/15 239/53 |
| 6,824,716 B2 | | 11/2004 | Liao et al. |
| 6,861,570 B1 * | | 3/2005 | Flick ........................ 602/41 |
| 6,887,488 B2 | | 5/2005 | Cui et al. |
| 7,048,963 B2 | | 5/2006 | Braithwaite et al. |
| 7,214,847 B1 * | | 5/2007 | Flick ........................ 602/48 |
| 7,230,153 B2 * | | 6/2007 | Flick ........................ 602/48 |
| 7,338,517 B2 | | 3/2008 | Yost et al. |
| 7,354,627 B2 | | 4/2008 | Pedrozo et al. |
| 7,596,415 B2 | | 9/2009 | Brabec |
| 7,890,179 B2 | | 2/2011 | Wiegmann et al. |
| 7,908,016 B2 | | 3/2011 | Atanasoska et al. |
| 8,028,647 B2 | | 10/2011 | McMurtry |
| 8,118,791 B2 * | | 2/2012 | Flick et al. ............... 604/304 |
| 8,449,514 B2 * | | 5/2013 | Flick ..................... 604/385.01 |
| 8,513,382 B2 | | 8/2013 | Paukshto et al. |
| 2003/0093107 A1 | | 5/2003 | Parsonage et al. |
| 2003/0139806 A1 | | 7/2003 | Haverkost et al. |
| 2003/0153965 A1 | | 8/2003 | Supronowicz et al. |
| 2003/0176827 A1 * | | 9/2003 | Chandra ................. A61L 15/18 602/48 |
| 2003/0212306 A1 * | | 11/2003 | Banik ................... A61F 2/0036 600/30 |
| 2004/0030276 A1 * | | 2/2004 | Flick ................. A61F 13/00063 602/41 |
| 2004/0037813 A1 * | | 2/2004 | Simpson ................... A61F 2/08 424/93.7 |
| 2005/0009178 A1 | | 1/2005 | Yost et al. |
| 2005/0019488 A1 | | 1/2005 | Braithwaite et al. |
| 2005/0038498 A1 * | | 2/2005 | Dubrow et al. ............ 623/1.15 |
| 2005/0240261 A1 | | 10/2005 | Rakos et al. |
| 2005/0267231 A1 | | 12/2005 | Pavlin |
| 2005/0284752 A1 * | | 12/2005 | Nitzan ..................... A61F 13/00 204/280 |
| 2006/0137688 A1 * | | 6/2006 | Aisenbrey ............. A61M 16/06 128/205.25 |
| 2006/0141015 A1 * | | 6/2006 | Tessier .................... A01N 59/16 424/443 |
| 2006/0198827 A1 | | 9/2006 | Levenberg |
| 2007/0041952 A1 | | 2/2007 | Guilak et al. |
| 2007/0123766 A1 | | 5/2007 | Whalen, III et al. |
| 2007/0207186 A1 * | | 9/2007 | Scanlon et al. ............... 424/424 |
| 2007/0244569 A1 * | | 10/2007 | Weber et al. ............... 623/23.75 |
| 2008/0115724 A1 | | 5/2008 | McMurtry et al. |
| 2008/0125687 A1 * | | 5/2008 | Flick et al. ................... 602/48 |
| 2008/0147199 A1 | | 6/2008 | Yost et al. |
| 2008/0254091 A1 | | 10/2008 | Lee et al. |
| 2008/0286447 A1 | | 11/2008 | Alden et al. |
| 2009/0069893 A1 | | 3/2009 | Paukshto et al. |
| 2009/0117087 A1 | | 5/2009 | Carroll et al. |
| 2009/0117807 A1 * | | 5/2009 | Uno et al. ..................... 445/3 |
| 2009/0124956 A1 * | | 5/2009 | Swetlin et al. ................. 604/8 |
| 2009/0192429 A1 * | | 7/2009 | Daniels .............. A61B 17/0057 602/43 |
| 2009/0252861 A1 * | | 10/2009 | Tessier .................... A01N 59/16 427/2.31 |
| 2009/0297581 A1 * | | 12/2009 | Atanasoska et al. ......... 424/423 |
| 2010/0036098 A1 | | 2/2010 | Paukshto et al. |
| 2010/0106233 A1 * | | 4/2010 | Grant et al. ................ 623/1.1 |
| 2011/0151563 A1 | | 6/2011 | Paukshto et al. |
| 2011/0217544 A1 * | | 9/2011 | Young et al. ................ 428/327 |
| 2013/0287744 A1 | | 10/2013 | Paukshto et al. |

FOREIGN PATENT DOCUMENTS

| | | |
|---|---|---|
| JP | 6-500802 | 1/1994 |
| JP | 2004-148014 A | 5/2004 |
| JP | 07-213597 | 8/2007 |
| JP | 2008-504921 | 2/2008 |
| JP | 09-122227 | 6/2009 |
| WO | WO 84/00548 A1 | 2/1984 |
| WO | WO 99/047188 | 9/1999 |
| WO | WO 00/61045 A1 | 10/2000 |
| WO | WO 2003/020316 A1 | 3/2003 |
| WO | WO 2004/050134 A2 | 6/2004 |
| WO | WO 2005/003300 A2 | 1/2005 |
| WO | WO 2005/081699 A2 | 9/2005 |
| WO | WO 2006/136817 A1 | 12/2006 |
| WO | WO 2007/028078 A2 | 3/2007 |
| WO | WO 2007/038601 A2 | 4/2007 |
| WO | WO 2008/034854 A1 | 3/2008 |
| WO | WO 2008/063631 | 5/2008 |
| WO | WO 2008/070166 A1 | 6/2008 |
| WO | WO 2008/131293 | 10/2008 |
| WO | WO 2009/064437 A1 | 5/2009 |
| WO | WO 2010/019625 A2 | 2/2010 |
| WO | WO 2010/022353 A1 * | 2/2010 ............ B28B 23/00 |
| WO | WO 2012/034110 | 3/2012 |

OTHER PUBLICATIONS

Wijnhoven, S. W.P. et al., "Nano-Silver—a Review of Available Data and Knowledge Gaps in Human and Environmental Risk Assesment," Nonotoxicology, Jun. 2009, 3(2), pp. 109-138.

International Search Report and Written Opinion in International Application No. PCT/US2011/044231, dated Mar. 20, 2012.

Besseau, L. et al., "Production of Ordered Collagen Matrices for Three-Dimensional Cell Culture," Biomaterials, 23, 2002, pp. 27-36.

Cisneros, D. et al., "Creating Ultrathin Nanoscopic Collagen Matrices for Biological and Biotechnological Applications", Wiley InterScience, 2007, vol. 3, No. 6, pp. 956-963.

Cowin, S., "Do Liquid Crystal-Like Flow Processors Occur in the Supramolecular Assembly of Biological Tissues?", J. Non-Newtonian Fluid Mech. 119, 2004, pp. 155-162.

Eglin, D. et al., "Type I Collagen, a Versatile Liquid Crystal Biological Template for Silica Structuration from Nano-to Microscopic Scales," The Royal Society of Chemistry. vol. 1, 2005, pp. 129-131.

(56) References Cited

OTHER PUBLICATIONS

Evans, H., et al. "Novel 3D Culture System for Study of Cardiac Myocyte Development," Am J. Physiol Heart Circ Physiol, vol. 285, 2003, pp. H570-H578.

Fennell, L., et al., "Thin Crystal Film Polarizers," Asia Display/ IDW, 2001, pp. 601-603.

Gobeaux, F., "Cooperative Ordering of Collagen Triple Helices in the Dense State", Langmuir 2007, vol. 23, pp. 6411-6417.

Guo, C. et al., "Flow and Magnetic Field Induced Collagen Alignment," Biomaterials, vol. 28, 2007, pp. 1105-1114.

Hansen, U. et al., "Material Properties of Biological Tissues Related to Joint Surgery," Current Orthopaedics, vol. 20, 2006, pp. 16-22.

Jiang, et al., Assembly of collagen into microribbons: effects of pH and electrolytes; Journal of Structural Biology, Academic Press, United States, vol. 148, No. 3, Dec. 1, 2004; pp. 268-278.

Knight, D. et al. "Biological Liquid Crystal Elastomers," Philosophical Transactions: Biological Sciences, vol. 357, No. 1418, Estomeric Proteins: Structures, Biomechanical Properties and Biological Roles., Feb. 12, 2002, pp. 155-163.

Koster, et al., Visualization of Flow-Aligned Type I Collagen Self-Assembly in Tunable pH Gradients; Langmuir, vol. 23, 2007, pp. 357-359.

Ledet, E. H. et al., "A Pilot Study to Evaluate the Effectiveness of Small Intestinal Submucosa Used to Repair Spinal Ligaments in the Goat," The Spine Journal, vol. 2, No. 3, May-Jun. 2002, pp. 188-196.

Martin, G. R. et al., "Behavior Of Cells on Highly Organized and Reconstituted Collagen Matices," the Cell, Bethesda MS USA, vol. 19, Dec. 13, 2008, p. 42.

Martin, R. et al., "Liquid Crystalline Ordering of Procollagen as a Determinant of Three-Dimensional Extracellular Matrix Architecture," J. Mol. Biol., vol. 301, 2000, pp. 11-17.

McPherson, T.B. et al., " Characterization of Fibronectin Derived from Porcine Small Intestinal Submucosa," Tissue Engineering, vol. 4, No. 1, 1998, pp. 75-83.

Ng, C. P. et al., "Fibroblast Alignment Under Interstitial Fluid Flow Using a Novel 3-D Tissue Culture Model," Am J. Physical Heart Circ. Physiol, vol. 284, Jan. 16, 2003, pp. H1771-H1777.

Paukshto, M., et al., "Optics of Sheared Liquid-Crystal Polarizer Based on Aqueous Dispersion of Dichroic-Dye Nano-Aggregates", Journal of the sid, 13/9, 2005, pp. 765-772.

Tan, W. et al. "Layer-by-Layer Microfluidics for Biometic Three-Dimensional Structures", Biomaterials, 2004, vol. 25. pp. 1355-1364.

Yoshizato, K. et al., "In Vitro Orientation of Fibroblasts and Myoblasts on Aligned Collagen Film", Develop., Growth and Differ., 23 (2), 1981, pp. 175-184.

Zhong, S. et al., "An Aligned Nanofibrous Collagen Scaffold by Electrospinning and its Effects on In Vitro Fibroblast Culture", Journal of Biomedical Materials Research Part A, 2006 Wiley Periodicals, Inc., pp. 456-463.

European Search Report and Opinion from European Application No. EP 08746355.0, dated Jun. 4, 2010, 8 pages.

European Examination Report in Application No. EP 08746355.0, dated Mar. 31, 2011.

European Examination Report in Application No. EP 08746355.0, dated Sep. 5, 2011.

International Search Report and Written Opinion for PCT/US2007/025037 dated Apr. 8, 2008.

International Search Report and Written Opinion for PCT/US2008/060919 dated Oct. 17, 2008.

International Search Report and Written Opinion in PCT/US2011/051135, dated Apr. 26, 2012.

Notice of Allowance in U.S. Appl. No. 12/539,563 dated Apr. 17, 2013.

Office Action in U.S. Appl. No. 12/539,563 dated Jan. 25, 2013.

Office Action in U.S. Appl. No. 12/539,563 dated Jun. 7, 2012.

Supplemental Notice of Allowability in U.S. Appl. No. 12/539,563 dated Jul. 2, 2013.

International Search Report and Written Opinion in PCT/US2009/053486, dated Mar. 26, 2010.

Notice of Allowance in U.S. Appl. No. 11/951,324 dated Mar. 20, 2012.

Notice of Allowance in U.S. Appl. No. 12/106,214 dated Jul. 2, 2012.

Office Action in U.S. Appl. No. 11/951,324 dated Sep. 7, 2011.

Office Action in U.S. Appl. No. 12/106,214 dated Aug. 5, 2011.

Office Action in U.S. Appl. No. 12/106,214 dated Jan. 19, 2012.

Australian Examination Report No. 1 in Application No. AU 2009282095, dated Mar. 7, 2014.

Australian Examination Report No. 2 in Application No. AU 2009282095, dated Mar. 16, 2015.

European Examination Report for European Application No. EP 09807197, dated May 26, 2014, 5 pages.

European Extended Search Report and Opinion for European Application No. EP 09807197, dated Jul. 10, 2013, 10 pages.

European Extended Search Report and Opinion for European Application No. EP 11824229.6, dated Jul. 17, 2014, 8 pages.

International Preliminary Report on Patentability in PCT/US2009/053486, dated Feb. 15, 2011, 5 pages.

International Preliminary Report on Patentability in PCT/US2011/051135, dated Mar. 12, 2013.

Japanese Office Action in Japanese Application No. 2011-523126 dated Sep. 29, 2015.

Japanese Office Action in Japanese Application No. 2011-523126 dated Feb. 10, 2014.

Kim et al., "Antimicrobial effect of silver-impregnated cellulose: potential for antimicrobial therapy", Journal of Biological Engineering. 3:20, 9 pgs., Dec. 2009.

\* cited by examiner

2D wire-grid - a model of connected nanowire network.

FIG. 4A   FIG. 4B

Silver nanowires impregnated into oriented fibrilar collagen matrix.

FIG. 5A   FIG. 5B

Conductive network of silver nanowires.

Day 6

Day 11

Fibroblasts are mostly aligned along the collagen fibrils.

Current map, U=10V. Distance between contacts 2mm.

CONDUCTIVE BIOPOLYMER IMPLANT FOR ENHANCING TISSUE REPAIR AND REGENERATION USING ELECTROMAGNETIC FIELDS

CROSS REFERENCE TO RELATED APPLICATIONS

This patent application claims the benefit of, and priority to, U.S. Provisional Patent application Ser. No. 61/364,759 filed on Jul. 15, 2010, the entire disclosure of which is hereby incorporated by reference.

TECHNICAL FIELD

Embodiments of the present invention relate generally to the field of tissue repair and regeneration. More specifically, embodiments of the present invention relate to medical devices, materials or constructs, such as conductive biopolymers, that enhance tissue repair and regeneration using electromagnetic fields.

BACKGROUND OF THE INVENTION

The regenerative capacity of injured tissues in adult humans is often limited, particularly with advancing age or diseases such as diabetes. Literature suggests that electrical, electrothermal, and electromechanical stimulation can enhance repair of wounds by stimulating vascularization, cell migration and cell proliferation as well as other processes. This process is often referred to as electrotherapy or electromagnetic therapy. The process depends on the application of an electric current via electrodes or an electromagnetic field to an area of a tissue, usually a wound. The flow of electricity is dependent upon the natural conductive processes of the treated tissues. Nerve repair is also reported to be stimulated by this process. In general, there are many clinical situations which would benefit from the directed application of electrotherapy, particularly if more effectively applied and if repair was directed and localized rather than random. Synthetic polymers have been used to enhance current flow to stimulate neurite outgrowth in tissue culture.

While it is possible to incorporate a variety of growth factors into these materials, there are advantages in accelerating repair and regeneration by enhancing the body's natural repair processes. Pulsed electromagnetic field therapy has been investigated, particularly with respect to bone repair. In brief, an electromagnetic field is generated with a device over the tissue site of interest and maintained for various periods of time. Among the results reported are more rapid healing of fractures, particularly recalcitrant fractures, induction of vascularization in ischemic tissues, and enhanced nerve growth. Further silver ions generated by the field may have the ability to suppress bacterial growth.

Methods to deposit collagen molecules in defined structures including aligned, woven and transparent materials convertible into bandages, sutures and multilayered structures for diverse indications are described in U.S. patent application Ser. Nos. 11/951,324, 11/986,263, 12/106,214, and 12/539,563, all of which are incorporated by reference herein in their entirety. One advantage of these collagen materials is that they closely approximate the natural structures of tissues, are biocompatible and induce the guided growth of cells attaching to them. The collagen materials appear to be an excellent substrate for applying mesenchymal and other stem cells to precise tissue sites. While these advances have been made, there is need for continued advancement and development of materials, constructs, implants and methods that promote and/or enhance tissue repair and regeneration.

SUMMARY OF THE INVENTION

Accordingly, some embodiments of the present disclosure provide medical devices, materials or constructs and methods that enhance and/or promote tissue repair and regeneration. In some embodiments a material or construct is provided comprised of: a composition of at least one biocompatible polymer (also referred to as "biopolymer") and one or more metal nanowires. A medical device is also described, comprising: at least one connected network of metal nanowires and at least one biocompatible polymer, and wherein the device exhibits electric conductivity in at least one direction across the device, and at least some of the network of metal nanowires are disposed in at least part of the biocompatible polymer. The concentration of the metal in the biocompatible polymer does not exceed a toxic level. In some embodiments the one or more network of metal nanowires have a concentration in the range from about 50 µg to 50 mg per liter. In some embodiments, the metal nanowires are at least partially aligned in at least one direction.

The at least one biocompatible polymer may be comprised of a fibrillar biopolymer. In this instance, the fibrillar biopolymer may have at least partially aligned fibrils in at least one direction. In some embodiments, this partial alignment of the fibrils substantially coincides with the partial alignment of the metal nanowires.

The at least one biocompatible polymer may be comprised of collagen. The one or more metal nanowires may be selected from any one or more of: Ag, Au, Pt, Ti, Fe, Ni, Si, V, Co, Cu or Zn and combinations thereof. In some embodiments, a plurality of metal nanowires are provided and the nanowires form a conductive net or network.

Of particular advantage, the one or more network metal nanowires can be aligned within the material in a desired orientation. In some embodiments the nanowires are aligned in the material to provide the material with conductivity in at least one direction. In some embodiments the metal nanowires are augmented and/or coated by fibrils of the biopolymer.

The concentration of metal nanowires present in the biocompatible polymer may be selected as desired. In some embodiments the concentration of the metal nanowires is below, or does not exceed, the level at which the metal would be considered toxic to a human or animal. In some embodiments, the concentration of the metal nanowires is sufficient to enable or promote antimicrobial properties of the material or medical device.

Methods are also provided according to additional aspects of the present invention. In one aspect, a method is described for producing a medical device having at least one connected network of metal nanowires and at least one biocompatible polymer wherein the device exhibits electric conductivity at least in one direction, comprising the steps of: depositing a water-based solution or gel containing metal nanowires on a first biocompatible polymer layer. Water is removed to form at least one connected metal nanowire network on the first biocompatible polymer layer. Then, the first biocompatible polymer layer with the metal nanowire network formed thereon is laminated to a second biocompatible layer to form a laminated construct. The laminated construct is then treated to enhance the connection between metal nanowires and to cross-link at least one biocompatible polymer included in the construct. In one example the laminated construct is treated by applying a dehydrothermal treatment. The method for producing a medical device according to the claim 12 wherein.

The water-based solution or gel may be comprised of a mixture of biopolymer and metal nanowires. In another example the solution or gel of metal nanowires may be comprised of at least one type of cross-linking molecules, glycoproteins, proteoglycans, bioactive or chemically active materials. Preferably the concentration of metal nanowires does not exceed a level toxic to humans or animals. In one example, the biopolymer solution or gel is comprised of an acidic water-based solution or acidic water-based gel of collagen.

In a different example, methods of making a material or construct are provided comprising the steps of: mixing one or more nanowires in a biopolymer solution to form a mixture having a concentration of the one or more nanowires of less than 50 mg per liter of biopolymer solution; and coating or depositing the mixture on a substrate under shear. In some embodiments, methods further comprise: drying the mixture on the substrate to preserve the orientation of the nanowires. Methods may further comprise laminating the material to form a multilayer stack. In some embodiments the material is laminated into a multilayer stack such that at least one interface between the multilayers has the mixture of deposited biopolymer solution and metal nanowires.

Additional components may be added to the mixture and then coated or deposited onto a substrate under a shear force. In some embodiments, the mixture of nanowires in a biopolymer solution further comprises one more of: crosslinking molecules, glycoproteins, proteoglycans, bioactive or chemically active materials, and mixtures thereof.

Of particular advantage, embodiments of the present invention find wide use as biomaterials, implants, constructs and medical devices. For example, and without limitation, materials or constructs of the present invention may be used for the treatment of wounds, or in the repair of connective tissues such as tendons, ligaments and the like. In some embodiments materials of the present invention are used to enhance repair and/or regeneration of tissues, such as the myocardium and the like to provide electrical connection between the areas in a heart isolated by scars.

In other embodiments, the device and materials of the present disclosure are used in the construction of a vascular conduit. Of particular advantage, flow through a vascular conduit of the present invention may be detected by detection of an electromagnetic field generated around the vascular conduit. Such vascular conduits may find use in a variety of applications, such as for example without limitation: as a bypass graft for vascular disease or for arteriovenous fistula formation for renal dialysis.

In further embodiment, the device of the present disclosure is used for the detection of flow through the vascular conduit described by detection of the electromagnetic field generated around the conduit.

Optionally, electromagnetically-active biodegradable, antibacterial material can be used to create devices inside of the body tissue, such as for examples: antennas, capacitors, conductors, and other piezoelectric and electromagnetic elements. In some embodiments the biocompatible polymer is aligned collagen, which is a good piezoelectric material.

In some embodiments, materials of the present invention are used for healing of tissue by application of pulse electromagnetic field. Moreover, methods are provided comprising applying a pulse electromagnetic field to a material comprised of at least one biopolymer and one or more nanowires to promote healing, repair and/or regeneration of tissue.

BRIEF DESCRIPTION OF THE FIGURES

The foregoing and other aspects of embodiments of the present invention will be apparent upon consideration of the following detailed description, taken in conjunction with the accompanying drawings, in which like reference characters refer to like parts throughout, and in which.

DETAILED DESCRIPTION OF THE INVENTION

It is to be understood that both the foregoing general description and the following description are exemplary and explanatory only and are not restrictive of the methods and devices described herein. In this application, the use of the singular includes the plural unless specifically state otherwise. Also, the use of "or" means "and/or" unless stated otherwise. Similarly, "comprise," "comprises," "comprising," "include," "includes," "including," "has," "have," and "having" are not intended to be limiting.

Example embodiments are described herein in the context of medical devices and biocompatible materials, and methods of making. Those of ordinary skill in the art will realize that the following description is illustrative only and is not intended to be in any way limiting. Other embodiments will readily suggest themselves to such skilled persons having the benefit of this disclosure. Reference will now be made in detail to various implementations of the example embodiments as illustrated in the accompanying drawings. The same reference indicators will be used to the extent possible throughout the drawings and the following description to refer to the same or like items.

Embodiments of the present invention describe methods to produce medical devices, constructs or implants comprised of compatible polymers with metal nanowires useful for implantation or applied to various tissues to enhance repair and regeneration when used with electrotherapy, among other uses. In some embodiments the biopolymer material or implants are comprised of collagen with silver nanowires. Of particular advantage the conductivity of such devices, materials or implants may be selectively controlled by inducing magnetic fields and thus inducing cellular activities to enhance or promote tissue healing as well as provide antibacterial properties and active electric stimulation.

For purposes of the following description, "Nanowire" means an elongated nanoparticle with an aspect ratio at least 2. In some embodiments, and without limitation, a typical aspect ratio is at least 100.

"Nanoparticle" means a particle which has at least one dimension less than 100 nm.

"Partially align(ed) nanowires" means that at least about 20% of the nanowires are oriented within about ±15 degree from a chosen direction.

Various embodiments of the medical devices and materials of the present invention are also referred to as constructs, scaffolds, collagen scaffolds, implants and/or biodevices. The terms biocompatible polymer and biopolymer are sometimes used interchangeably.

In some embodiments the one or more metal nanowires have a concentration in the range from about 50 µg to 50 mg per liter. In some embodiments, the metal nanowires are at least partially aligned in at least one direction.

Figure 1:
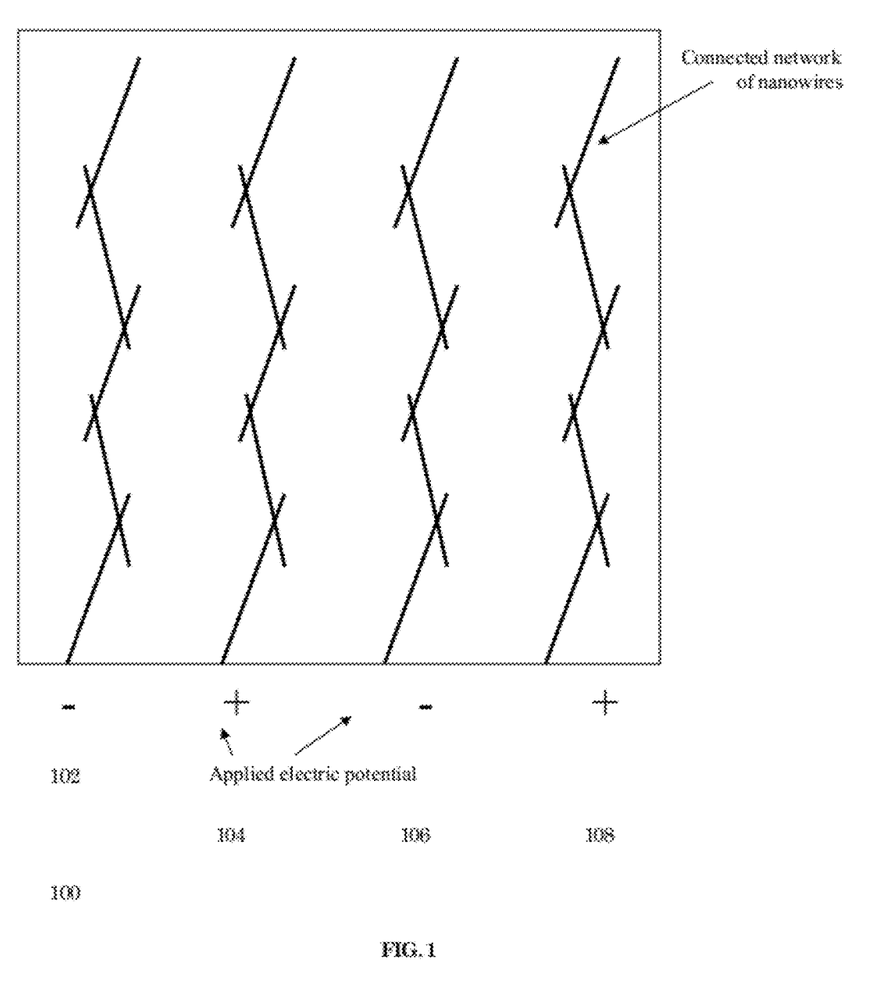
FIG. 1 is a schematic drawing illustrating a connected network of metal nanowires according to some embodiments of the present disclosure.

FIG. 1 is a simplified schematic drawing illustrating one example of a connected network of metal nanowires 100. As used herein the term "connected" sometimes refers to electrical connection or electrical coupling between one or more of the individual metal nanowires as shown in FIG. 1. In this example a plurality of connected networks 102, 104, 106, 108 are shown and the networks are substantially oriented in a similar direction. An electric potential of alternating polarity is applied to each of the networks. Those of skill in the art will recognize that other arrangements and configurations are possible given the teaching herein, and that all such modifications are within the scope of the present disclosure and appended claims.

The at least one biocompatible polymer may be comprised of a fibrillar biopolymer. In this instance, the fibrillar biopolymer may have at least partially aligned fibrils in at least one direction. In some embodiments, this partial alignment of the fibrils substantially coincides with the partial alignment of the nanowires.

The at least one biopolymer may be comprised of collagen, such as but not limited to collagen 1. The one or more metal nanowires may be selected from any one or more of: Ag, Au, Pt, Ti, Fe, Ni, Si, V, Co, Cu or Zn, and combinations thereof. In one example the metal nanowires are comprised of silver. In some embodiments, a plurality of metal nanowires are provided and the nanowires form a conductive net or network.

Of particular advantage, the one or more metal nanowires can be aligned within the material in a desired orientation. In some embodiments the nanowires are aligned in the material to provide the material with conductivity in at least one direction. The metal nanowires are augmented or coated by fibrils of the biopolymer.

The concentration of metal nanowires present in the biopolymer may be selected as desired. In some embodiments the concentration of the metal nanowires is below, or does not exceed, the level at which the metal would be considered toxic to a human or animal. In some embodiments, the concentration of the metal nanowires is sufficient to enable antimicrobial properties of the material.

Additional components may be added, for example the mixture of nanowires in the biocompatible polymer may further include one more of: crosslinking molecules, glycoproteins, proteoglycans, bioactive or chemically active materials, or mixtures thereof.

Figure 2:
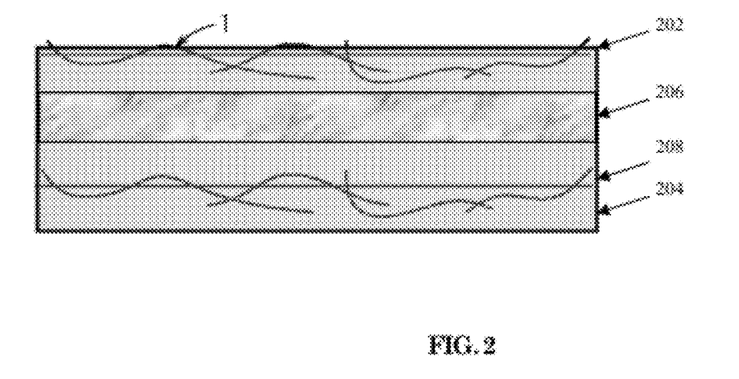
FIG. 2 is a cross-sectional view of multilayered device or construct showing two conductive layers formed by metal nanowire networks according to some embodiments of the present disclosure.

FIG. 2 shows a cross-sectional view of multilayered device or construct 200 showing two conductive layers formed by metal nanowire networks according to some embodiments of the present disclosure. In one example, the multilayered device is broadly comprised of two conductive layers 202, 204 separated by an insulator 206. Top conductive layer 202 has formed therein a network of metal nanowires 1 formed primarily near the top surface of the layer 202. Bottom conductive layer 204 is a biopolymer and has a network of metal nanowires 208 formed therein that are substantially encapsulated within the layer 204. Preferably, layer 204 exhibits a low metal ion diffusion speed.

In one example illustration we have incorporated silver nanowires into reconstituted collagen constructs. The ratio of collagen to silver nanowires can be varied depending on the usage of the material. Silver nanowires can be dispersed throughout the collagen or instead deposited in a layer on the surface of the collagen or between collagen sheets. Application of an external instrument to generate an electric current can be achieved throughout the collagen as in an application for wound healing. Alternatively, the collagen/silver nanowire construct can be assembled into a suture-like construct and inserted, for example, in the heart to act as a pacemaker or into ischemic tissue to induce vascularization. Also, silver nanowire constructs can be assembled into tubes to act to accelerate nerve regeneration, other constructs are made for specific uses in tissues to enhance repair and restore function.

There are two important limitations for the concentration of silver nanowires in the biopolymer. They are: (1) silver (Ag) toxicity level measured in mg/g (ratio of the nanowire amount to the weight of the biopolymer or scaffold material), which is reported to be 10 mg/g; and (2) the silver antimicrobial level measured in mg/g (ratio of the nanowire amount to the weight of the biopolymer or scaffold material), which is reported to be 0.01 mg/g.

Figure 3:
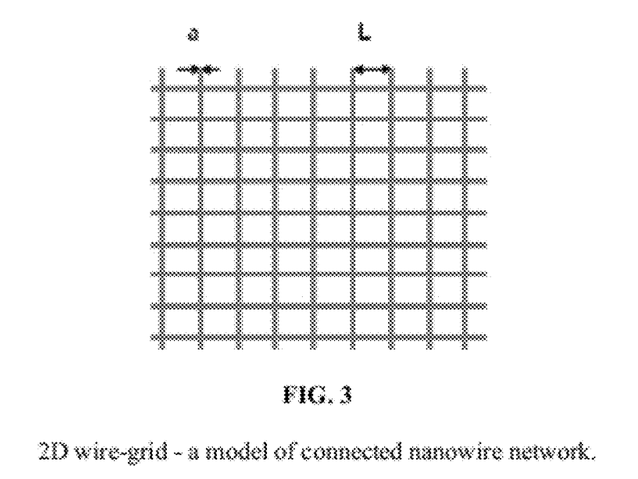
FIG. 3 depicts a 2-D wire grid model of a connected nanowire network according to another embodiment of the present disclosure.

One model of a connected nanowire network is a 2D wire-grid, as shown in FIG. 3, where L is the length of the nanowires and a is the diameter of nanowires.

The corresponding concentration of the silver nanowires in the collagen scaffold of the thickness h is:

$$3.7 * \pi * \frac{a^2}{L * h}$$

where the dry collagen density is 1.42 g/cm3 and silver density is 10.5 g/cm3. Thus, the electrically conductive collagen scaffold that includes this 2D wire-grid has antimicrobial effect and has no toxicity if:

$$10^{-5} \leq 3.7 * \pi * \frac{a^2}{L * h} \leq 10^{-2}.$$

In the case of collagen scaffold with thickness h=5 micron, L=10 micron, and a=50 nm we have:

$$3.7 * \pi * \frac{a^2}{L * h} = 0.00058.$$

Therefore this collagen scaffold has electrical conductivity and antimicrobial properties. The concentration of silver is significantly below the toxic level. This design is possible because the silver nanowires have a high aspect ratio (200).

The sheet resistance of the 2D silver wire-grid model is equal to:

$$R = \frac{4\rho_e L}{\pi a^2}$$

where $\rho_e = 1.6 \times 10^{-8}$ Ω-m. In the considered model we have L=10 micron, a=50 nm, and therefore R=81.6 Ω/sq. The ideal contact between nanowires is assumed in this model. In an operating system one would assume at least one order of magnitude higher resistance for the same concentration of nanowires as in the model.

It should be noted that a variety of other metal nanowires can be introduced into similar constructs according to the present teaching.

Embodiments of the present invention are useful in a number of applications. In one example, the material may be used as a sheet of material, such that the invention can be applied to cover a dermal wound or the surface of a fracture. The material may be used as a tube, wherein the inventive material can be used as a nerve guide for the repair of damaged nerves. The material my be used as a suture, and can be inserted into failing and/or ischemic tissues such as the kidney, heart, or muscle to enhance blood flow and repair as well as enhance function, for example, to induce insulin secretion by the pancreas or contraction of the heart muscles.

Flowing blood contains electrolytes with positive and negative charges. The flow of electrolytes through the silver wire impregnated conduit will induce a small electromagnetic field. Such fields are known to enhance healing. Accordingly the silvered conduit will promote endothelial regeneration, thereby accelerating the resurfacing of the lumen of the conduit by a monolayer of endothelial cells. Restoration of a normal and complete endothelial lining will promote vascular homeostasis, as the endothelium produces panoply of paracrine factors that induce vasorelaxation; that inhibit abnormal vascular smooth muscle growth and re-narrowing of the lumen; that inhibit immune cell infiltration and inflammation; and that prevent thrombus from forming on the vessel wall and obstructing blood flow.

Alternatively, an external magnetic field can be imposed on the conduit, causing a weak electrical current to be generated in the silver wires of the conduit. Weak electrical currents are known to enhance healing. It is expected that in this situation, the endothelial monolayer would be regenerated at an accelerated rate. The rapid endothelialization of the conduit would preserve its patency, due to the mechanisms described above (i.e. inhibition of aberrant vascular smooth muscle cell growth, platelet adherence and immune cell infiltration).

The weak magnetic field generated by the blood flowing through the conduit, is proportional to the amount of electrolyte solution flowing through the conduit. Since the concentration of electrolytes in the blood are tightly regulated in a narrow range, the strength of the magnetic field is directly proportional to blood flow. It is possible to measure the strength of the magnetic field by external devices. Because the strength of the magnetic field is dependent upon blood flow, its detection and quantification permits an assessment of blood flow through the conduit. Since the flow of blood through the conduit is dependent upon its patency, the magnetic field is an indication of the patency of the conduit. Furthermore, since the flow of blood through the conduit is directly related to the fourth power of the internal radius of the conduit, one can determine if the internal radius of the conduit has become smaller (as would occur with the adherence of thrombus, or with abnormal thickening of the vessel wall, ie. restenosis).

EXPERIMENTAL

A number of experiments were conducted as described below. These examples are shown for illustration purposes only and are not intended to limit the invention in any way.

Figure 4A:
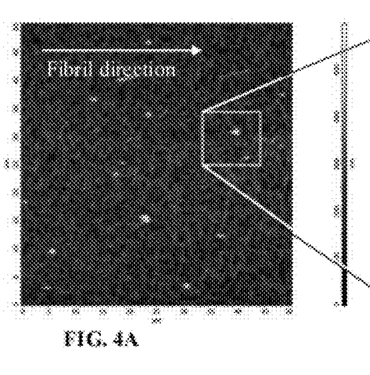
FIGS. 4A and 4B are atomic force microscope (AFM) measurements of a collagen material with silver nanowires formed therein according to some embodiments of the present disclosure.
Figure 4B:
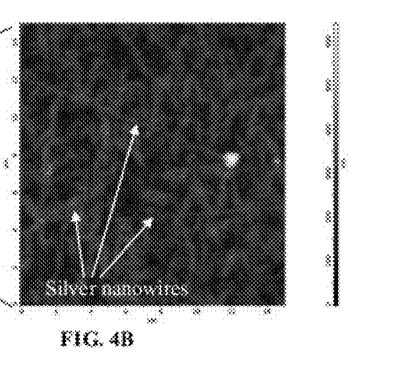
Figure 5A:
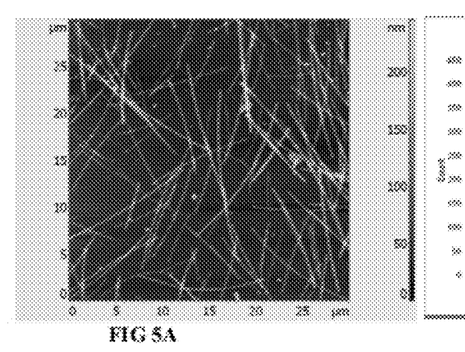
FIG. 5A is an AFM of a conductive network of silver nanowires formed in a material according to some embodiments of the present disclosure.
Figure 5B:
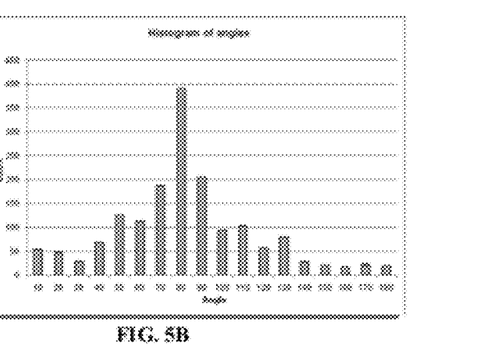
FIG. 5B illustrates a histogram of angles of the silver nanowires in the material of FIG. 4A.
Figure 6A:
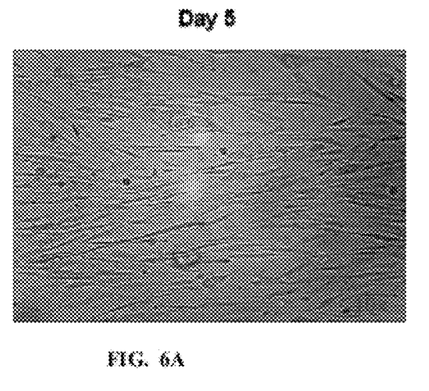
FIGS. 6A and 6B are photographs showing human fibroblast cells aligned on a fibilar collagen material with silver nanowires according to embodiments of the present disclosure at day 5 and day 11 of growth, respectively.
Figure 6B:
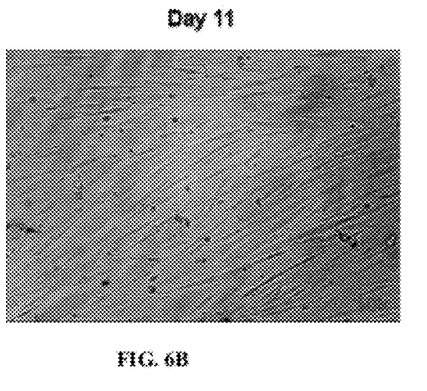

Examples of multilayer collagen scaffolds with silver nanowires are shown in the figures. FIGS. 4A and 4B are AFM measurements of impregnated nanowires in the tendon-like collagen layer. FIGS. 5A and 5B are AFM measurements of connected network of silver nanowires on the interface of one layer. Photos of human fibroblast cells plated on aligned fibrillar collagen matrix with impregnated silver nanowires are presented in FIGS. 6A and 6B, and show a high degree of cell alignment indicating that the impregnated nanowires have not altered the aligned fibrillar structure of the collagen.

Figure 7A:
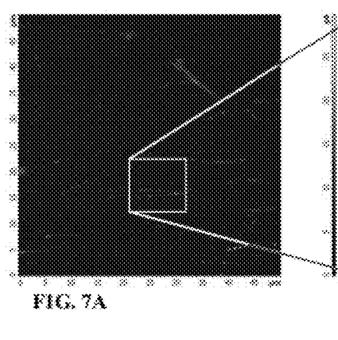
FIGS. 7A and 7B illustrate electrical properties of a collagen material scaffold with silver nanowires formed therein according to some embodiments of the present disclosure.
Figure 7B:
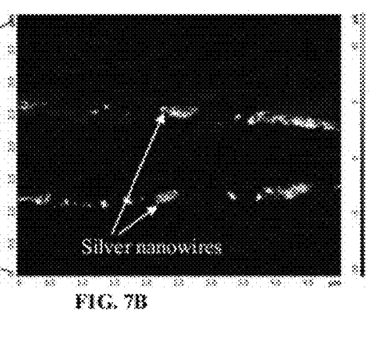

Electrical properties of the collagen scaffold with impregnated silver nanowires are shown in FIGS. 7A and 7B. The nanowires are augmented by collagen fibrils therefore only the traces of nanowires are seen at the map of the electrical current distribution.

Typical sheet resistance of the scaffold with silver nanowires varies from 100 Ω/sq (interface deposition—FIGS. 5A and 5B) to 100 kΩ/sq (impregnated coating—FIGS. 4A and 4B).

The foregoing methods, materials, constructs and description are intended to be illustrative. In view of the teachings provided herein, other approaches will be evident to those of skill in the relevant art, and such approaches are intended to fall within the scope of the present invention.

We claim:

1. A medical device, comprising:
at least one connected network of metal nanowires; and
at least one biocompatible fibrillar biopolymer, wherein the device exhibits electric conductivity in at least one direction across the device, and at least some of the network of metal nanowires are encapsulated in at least part of the biocompatible fibrillar biopolymer having at least partially aligned fibrils in at least one direction which coincides with an alignment of the encapsulated metal nanowires and the network of nanowires span a majority of the length of the biocompatible fibrillar biopolymer, forming a layer with sheet resistance less than 100 kΩ/sq, said metal nanowires consist essentially of metal, said metal nanowires have a cross-section dimension of less than 100 nm, and the concentration of said metal in the biocompatible fibrillar biopolymer is less than 1 wt %.

2. The medical device of claim 1 wherein the device is biocompatible with body tissue.

3. The medical device of claim 1 wherein the concentration of metal nanowires is in the range from 50 μg to 50 mg per liter.

4. The medical device of claim 1 wherein said biocompatible fibrillar biopolymer is collagen.

5. The medical device of claim 1 wherein the concentration of metal nanowires is high enough to enable antimicrobial properties of the device.

6. The medical device according to claim 1, further comprising: the at least one connected network of metal nanowires located between two biocompatible fibrillar biopolymer layers, and made by a method comprising the steps of:
- depositing a water-based solution or gel containing metal nanowires on a first biocompatible fibrillar biopolymer layer;
- removing water from the water-based solution or gel to form the at least one connected network of metal nanowires on the first biocompatible fibrillar biopolymer layer;
- laminating the first biocompatible fibrillar biopolymer layer with the at least one connected network of metal nanowires thereon to a second biocompatible fibrillar biopolymer layer to form a laminated construct; and
- treating the laminated construct to enhance the connection between metal nanowires and to cross-link at least one of the biocompatible fibrillar biopolymer layers included in the construct.

7. The medical device according to the claim 6 wherein the water-based solution or gel is a water solution of metal nanowires.

8. The medical device according to the claim 7 wherein the water-based solution or gel further comprises at least one of: cross-linking molecules, glycoproteins, proteoglycans, bioactive or chemically active materials.

9. The medical device according to the claim 6 wherein the water-based solution or gel is a mixture of biopolymer and metal nanowires.

10. The medical device according to the claim 9 wherein the water-based solution or gel is an acidic water-based solution or acidic water-based gel of collagen.

11. The medical device according to the claim 6 wherein the second biocompatible fibrillar biopolymer layer is comprised of one or more biocompatible fibrillar biopolymers and metal nanowires.

12. The medical device according to the claim 6 wherein the at least one connected network of metal nanowires is augmented by fibrils of the biopolymer of at least one of the first and second biocompatible fibrillar biopolymer layers.

13. The medical device according to the claim 6 wherein the at least one connected network of metal nanowires is encapsulated by one or more of the first or second biocompatible fibrillar biopolymer layers.

14. The medical device according to the claim 6 wherein the laminated construct comprises a multilayer stack wherein at least one interface between layers has formed thereon a deposited suspension of metal nanowires.

15. The medical device according to the claim 6 wherein the treating step is a dehydrothermal treatment.

* * * * *